Jan. 21, 1936. A. F. WATKINS Plant Pat. 162
ROSE
Filed Aug. 22, 1935
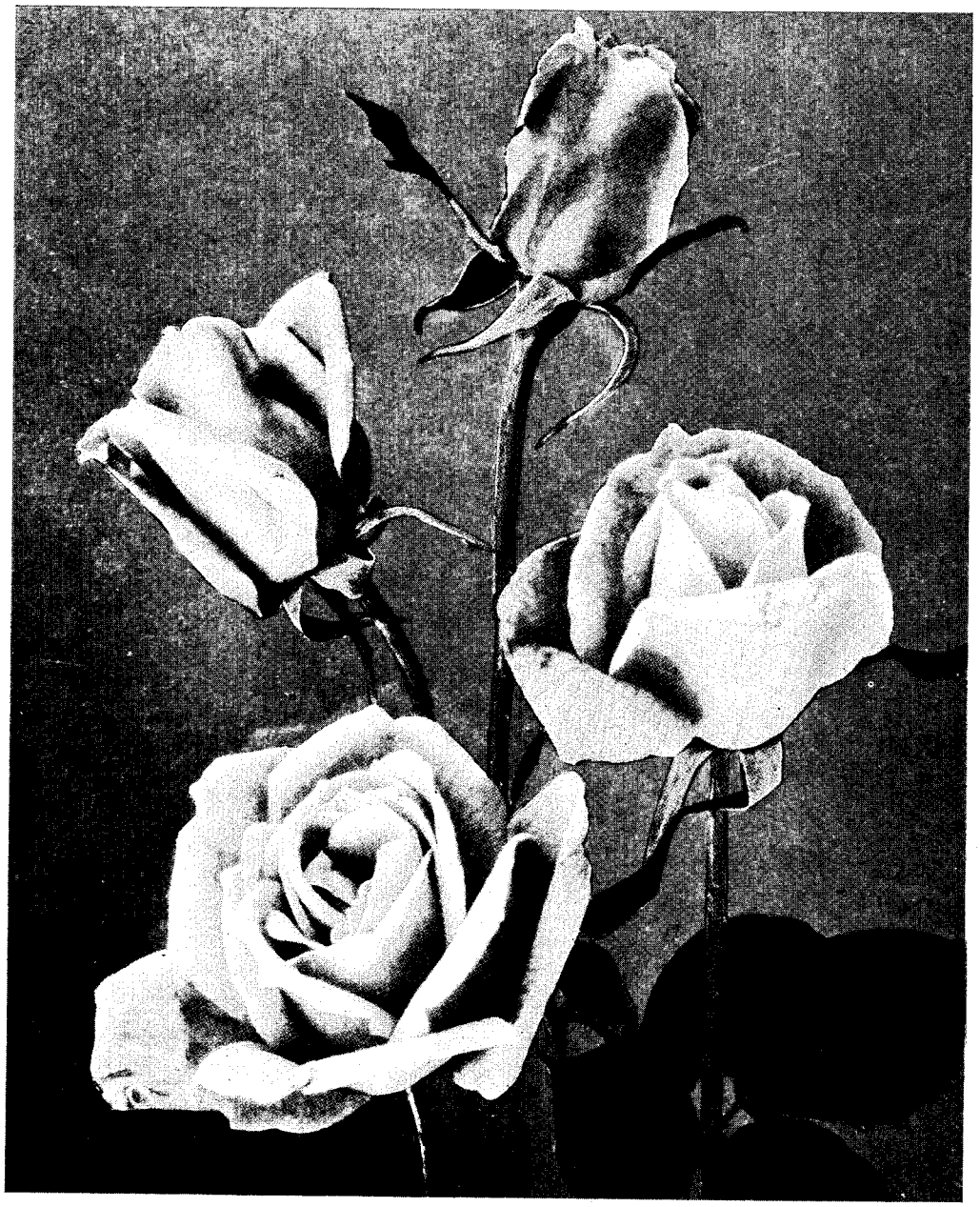
Inventor
Archibald Flint Watkins
By Robert Cobb
Attorney

UNITED STATES PATENT OFFICE

162

ROSE

Archibald Flint Watkins, Tyler, Tex., assignor to
Dixie Rose Nursery, Tyler, Tex.

Application August 22, 1935, Serial No. 37,408

1 Claim. (Cl. 47—61)

The present discovery relates to a new and distinct rose plant originating as a sport of the well-known, multi-colored, hybrid tea rose "President Herbert Hoover".

This parent rose referred to is well recognized as a universally satisfactory garden rose and in view of the fact that the present offspring possesses many of the attributes of its parent, a novel variety of great value becomes available not only as a garden rose, but also as a cut flower variety for forking.

My new rose is characterized by the novel coloring of its flower which is a blood red in the bud, changing to amaranth red when open, paling somewhat in the center, the general tonality being somewhat similar to the "Mary Hart" (Plant Patent No. 8) but differing therefrom by greater brilliancy.

The present rose has been asexually reproduced and the characteristics thereof are found to be fixed.

In detail, my new rose is described as follows, all references to color being in accordance with the Gravereaux system.

Parentage:
Sport of "President Herbert Hoover".
Classification:
*Botanic and commercial.*—Hybrid Tea.

*Flower*

Blooming habit:
Continuous.
Bud:
*Size.*—Very large.
*Form.*—Very long, pointed; unaffected by wet or hot weather.
*Color.*—When sepals first divide—blood red when petals begin to unfurl—blood red when half blown: inside of petals—amaranth red; reserve side of petals—blood red.
*Sepals.*—Serrated; curl back when bud is half open.
*Calyx.*—Shape—funnel. Size—large. Aspect—smooth. Odor when rubbed—none.
*Peduncle.*—Length—very long. Aspect—rough. Color—green. Strength—stiff; heavy.
*Opening.*—Opens well and is not affected by adverse conditions.
Bloom:
*Size.*—Very large; average size when fully expanded 4 to 4½ inches.
*Borne.*—Singly or several together.
*Stems.*—Long; strong.
*Form.*—When first open cupped; retains its form to the end.
*Petalage.*—Double (full but open center); number of petals under normal conditions 25 to 30.
*Color.*—Center of flower—amaranth red. Outer petals—blood red. Base of petals (aiglet) pink. Inside of petals—cerise red. Reverse of petals—blood red. General tonality from a distance—blood red toning to pink in center.
*Variegations.*—None.
*Discoloration.*—Slightly lighter third day.
Petals:
*Texture.*—Thick; unaffected by wet or hot weather.
*Appearance.*—Inside and outside satiny.
*Form.*—Round.
*Arrangement.*—Imbricated; petaloids in center few and small.
*Persistence.*—Drop off cleanly.
*Fragrance.*—Moderate. Nature—fruity (Russet apple).
*Lasting quality.*—On plant and as cut flower very long.
Genital organs:
*Stamens, anthers.*—Large, many. Color—yellow. Arrangement—regular around styles.
*Stamens, filaments (threads).*—Medium. Color—reddish.
*Pollen.*—Lemon yellow.
*Styles.*—Bunched; even medium length; heavy.
*Stigmas.*—Yellow color.
*Ovaries.*—All enclosed in calyx.
Fruit:
Variety is fertile with its own pollen.
*Form.*—Ovoid, flat headed.
*Aspect.*—Smooth.
*Color at maturity.*—Orange.
*Sepals.*—Caducous (soon falling).

*Plant*

Form:
Bush.
Growth:
Very vigorous, compact.
Foliage:
Generally five leaflets.
*Size.*—Large.
*Quantity.*—Normal.
*Color.*—New foliage—upper side bronzy, under side reddish. Old foliage—upper side dark green, under side normal green.
*Shape.*—Oval pointed.

*Texture.*—Upper side leathery, under side rough. Ribs and veins ordinary.

*Edge.*—Serrated (saw toothed).

*Serrations.*—Single, large.

*Rachis.*—Color reddish, under side smooth.

*Stipules.*—Medium length, smooth.

*Disease resistance.*—Resistant.

Wood:

*New wood.*—Reddish color.

*Old wood.*—Brown color and rough bark.

Thorns: (Divided into thorns, prickles, and short needles.)

*Thorns.*—Quantity—on main stalks from base, ordinary; on laterals from stalk, ordinary. Form—broad base; medium length; hooked downward. Color when young—red. Position—irregular.

*Prickles.*—Quantity—on main stalks, few on laterals, none. Color—brown.

*Short Needles.*—Quantity—on main stalks, none; on laterals, none.

I claim:

A new and distinct hybrid tea rose plant, characterized by the red color of its flower as shown and described.

ARCHIBALD FLINT WATKINS.